US 8,323,632 B2

(12) United States Patent
Zhao et al.

(10) Patent No.: US 8,323,632 B2
(45) Date of Patent: *Dec. 4, 2012

(54) MULTI-ARM POLYPEPTIDE-POLY(ETHYLENE GLYCOL) BLOCK COPOLYMERS AS DRUG DELIVERY VEHICLES

(75) Inventors: Xuan Zhao, Beijing (CN); Zhongxu Ren, Madison, AL (US); Kazunori Emoto, Broomfield, CO (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,144

(22) Filed: Jun. 2, 2011

(65) Prior Publication Data
US 2011/0237747 A1 Sep. 29, 2011

Related U.S. Application Data

(63) Continuation of application No. 11/985,443, filed on Nov. 14, 2007, now Pat. No. 7,976,834, which is a continuation of application No. 10/746,567, filed on Dec. 24, 2003, now Pat. No. 7,316,811.

(60) Provisional application No. 60/437,372, filed on Dec. 30, 2002.

(51) Int. Cl.
*A61K 31/79* (2006.01)

(52) U.S. Cl. ............... 424/78.27; 424/78.08; 424/78.17; 424/78.35; 424/78.37

(58) Field of Classification Search .................. None
See application file for complete search history.

(56) References Cited

U.S. PATENT DOCUMENTS

| | | | |
|---|---|---|---|
| 5,395,885 | A | 3/1995 | Kennedy et al. |
| 5,594,072 | A | 1/1997 | Handlin, Jr. et al. |
| 5,618,528 | A | 4/1997 | Cooper et al. |
| 6,150,468 | A | 11/2000 | Schoenberg et al. |
| 6,228,945 | B1 | 5/2001 | Kennedy et al. |
| 6,328,988 | B1 | 12/2001 | Uhrich |
| 6,469,132 | B1 | 10/2002 | Eisenberg et al. |
| 7,316,811 | B2 | 1/2008 | Zhao et al. |
| 7,976,834 | B2 | 7/2011 | Zhao et al. |
| 2002/0032309 | A1 | 3/2002 | Deming et al. |
| 2002/0041898 | A1 | 4/2002 | Unger et al. |
| 2004/0161403 | A1 | 8/2004 | Zhao et al. |

FOREIGN PATENT DOCUMENTS

| | | |
|---|---|---|
| CA | 2 377 211 | 1/2001 |
| WO | WO 95/03356 | 2/1995 |
| WO | WO 00/65024 | 11/2000 |
| WO | WO 01/49268 | 7/2001 |
| WO | WO 03/055935 | 7/2003 |

OTHER PUBLICATIONS

Adams, et al., "Amphiphilic Block Copolymers for Drug Delivery," J. of Pharm. Sci., vol. 92, No. 7, pp. 1343-1355, (Jul. 2003).
Anderson, et al., "Folic acid-PEO-labeled liposomes to improve gastrointestinal absorption of encapsulated agents," J. of Contr. Rel., vol. 60, pp. 189-198, (1999).
Breitenbach, et al., "Branched biodegradable polyesters for parenteral drug delivery systems," J. of Contr. Rel., vol. 64, pp. 167-178, (2000).
Caponetti, et al., "Microparticles of Novel Branched Copolymers of Lactic Acid and Amino Acids: Preparation and Characterization ," J. of Pharm. Sci., vol. 88, No. 1, pp. 136-141, (Jan. 1999).
Dagani, "Chemists Explore Potential of Dendritic Macromolecules as Functional Materials Hyperbranched polymers and dendrimers are being eyed as drug-delivery agents, micelle mimics, and nanoscale building blocks," Chem. & Engineering News, (Jun. 3, 1996).
Henry, "Block Polypeptide Hydrogels: Material formed at low concentration could find use in tissue engineering," Chem. & Engineering News, p. 14, (May 27, 2002).
Jeong, et al., "New biodegradable polymers for Injectable drug delivery systems," J. of Contr. Rel., vol. 62, pp. 109-114, (1999).
La, et al., "Preparation and Characterization of the Micelle-Forming Polymeric Drug Indomethacin-Incorporated Poly(ethylene oxide)-Poly(B-benzyl L-aspartate) Block Copolymers Micelles," J. of Pharm. Sci., vol. 85, No. 1, pp. 85-90, (Jan. 1996).
Lavasanifar, et al., "Block Copolymers Micelles for the Encapsulation and Delivery of Amphotericin B," Pharmceu. Res., vol. 19, No. 4, pp. 418-422, (Apr. 2002).
Lavasanifar, et al., "The effect of fatty acid substitution on the in vitro release of amphotericin B from micelles composed of poly(ethylene oxide)-block-poly(N-hexyl stearate-L-aspartamide)," J. of Contr. Rel., vol. 79, pp. 165-172, (2002).
Lavasanifar, et al., "Poly(ethylene oxide)-block-poly(L-amino acid) micelles for drug delivery," Adv. Drug Del. Rev., vol. 54, pp. 169-190, (2002).
Liu, et al., "Water-soluble dendritic unimolecular micelles: Their potential as drug delivery agents," J. of Contr. Rel., vol. 65, pp. 121-131, (2000).
Petersen, et al., "The macrostopper-Route: A New Synthesis Concept Leading Exclusively to Diblock Copolymers with Enhanced DNA Condensation Potential," Macromolecules, vol. 35, pp. 9854-9856, (2002).
Veronese, "Peptide and protein PEGylation: a review of problems and solutions," Biomaterials, vol. 22, pp. 405-417, (2001).
Yarnell, "22nd Amino Acid Identified: Methanogen uses stop codon to genetically encode L-Pyrrolysine," Chem. & Engineering News, p. 13, (May 27, 2002).

(Continued)

*Primary Examiner* — James Rogers
(74) *Attorney, Agent, or Firm* — Mark A. Wilson

(57) ABSTRACT

The invention provides a multi-arm block copolymer for use in delivering a variety of bioactive agents. The copolymer of the invention contains a central core from which extend multiple (3 or more) copolymer arms. Each copolymer arm possesses an inner polypeptide segment and an outer hydrophilic polymer segment. Thus, the overall structure of the copolymer comprises an inner core region that includes the central core and the inner polypeptide segment, while the outer core region is hydrophilic in nature. The multi-arm copolymer of the invention is particularly useful for delivery of biologically active agents that can be entrapped within the inner core region.

26 Claims, 2 Drawing Sheets

OTHER PUBLICATIONS

Shearwater Polymers, Inc., Polyethylene Glycol and Derivatives, 50 pages, (Catalog—Mar. 1995).

Shearwater Polymers, Inc., Polyethylene Glycol and Derivatives, 55 pages, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, 20 pages, (Catalog—Jul. 2001).

European Examination Report in European Application No. 03814969.6 dated Oct. 13, 2005.

European Examination Report in European Application No. 03814969.6 dated May 15, 2006.

European Examination Report in European Application No. 03814969.6 dated Apr. 17, 2008.

PCT International Search Report in PCT Application No. PCT/US2003/41332 mail date May 11, 2004.

Australian Examiner's First Report corresponding to Australian Patent Application No. 2003300380 dated Sep. 28, 2007.

Canadian Examination Report corresponding to Canadian Patent Application No. 2,508,015 dated Oct. 22, 2010.

Chinese Notification of the First Office Action corresponding to Chinese Patent Application No. 200380107984.3 date of notification Feb. 2, 2007.

Indian First Examination Report corresponding to Indian Patent Application No. 2434/DELNP/2005 dated Oct. 26, 2007.

Indian Examination Report corresponding to Indian Patent Application No. 2434/DELNP/2005 dated Oct. 24, 2008.

Japanese Notice of Reasons for Rejection corresponding to Japanese Patent Application No. 2004-565733 mailing date Jun. 30, 2009.

Korean Notice of Grounds for Rejection corresponding to Korean Patent Application No. 2005-7012445 issuance date Aug. 24, 2010.

Mexican First Office Action corresponding to Mexican Patent Application No. PA/a/2005/007146 dated Jun. 11, 2009.

— Poly(amino acid)
---- PEG

— Poly(amino acid)
---- PEG

MULTI-ARM POLYPEPTIDE-POLY(ETHYLENE GLYCOL) BLOCK COPOLYMERS AS DRUG DELIVERY VEHICLES

CROSS REFERENCE TO RELATED APPLICATIONS

This application is a continuation of U.S. patent application Ser. No. 11/985,443, filed Nov. 14, 2007, now issued as U.S. Pat. No. 7,976,834, which is a continuation of U.S. patent application Ser. No. 10/746,567, filed Dec. 24, 2003, now issued as U.S. Pat. No. 7,316,811, which claims the benefit of U.S. Provisional Patent Application Ser. No. 60/437,372 filed on Dec. 30, 2002, the disclosures of each are hereby incorporated herein by reference in their entireties.

FIELD OF THE INVENTION

The invention relates to multi-arm copolymers and methods of making and using such copolymers as, for example, drug delivery vehicles.

BACKGROUND OF THE INVENTION

The development of effective drug delivery vehicles continues to present a challenge for drug manufacturers. Many bioactive agents, while displaying potent in vivo activity, are hampered by drawbacks such as in vivo degradation, rapid elimination from the body, low aqueous solubility, and systemic toxicity. Several approaches have been suggested to overcome these drawbacks. Such approaches include, for example, co-administering a bioactive agent with a surfactant, providing the bioactive agent in a liposomal formulation, providing targeting to a specific tissue by employing an antibody, and formulating the bioactive agent within a micelle. Each approach, however, does not fully address the problems encountered with the specific active agent and/or generates additional challenges.

Pharmaceutical grade surfactants, such as Tween 80 or Cremophor®, have been widely used in formulations to compensate for the low aqueous solubility of hydrophobic drugs. These surfactants solubilize hydrophobic drugs by forming micellar structures in aqueous media. Unfortunately, these surfactants have been associated with severe allergic reactions and hypersensitivity when administered to patients (Kris et al. (1986) *Cancer Treatment REP* 70:5. In addition, micellar drug carriers often disintegrate upon administration to a patient because the concentration of the component forming the micelle falls below its critical micelle concentration (CMC). Once the micelle disintegrates, there is a rapid and uncontrolled release of the drug, thereby often rendering this approach to drug delivery as impracticable.

Liposomal formulations are made up of phospholipids that form liposomes. Upon administration to a patient, the liposomes are taken up by macrophages of the reticulo-endothelial system ("RES"). High levels are often found in the liver and spleen, even when the liposomes are modified to possess "stealth" characteristics by coating them with poly(ethylene glycol) ("PEG"). Even PEG-coated "stealth" liposomes, however, possess undesirable side effects. In particular, such PEG-coated liposomes are known to indiscriminately move from the blood vessels into tissues, a process known as "extravasation." As a result, higher doses of liposome-encapsulated drug must be administered to achieve a desired therapeutic effect.

Targeted delivery approaches, e.g., using antibodies to deliver drugs such as anticancer agents, have been employed for localized treatment of diseases such as cancer. Unfortunately, the receptors being targeting on the tumor cells are often present on healthy cells as well. Thus, antibody-targeting approaches often lack the specificity or selectivity necessary for providing an optimized method for delivering a bioactive agent.

Still other approaches have been suggested for delivering drugs. For example, water-soluble polymers such as poly(ethylene glycol) have been covalently attached to drugs to form polymer-drug conjugates. Such conjugates often possess improved water solubility, enhanced in vivo stability, and an improved therapeutic index in comparison to the unconjugated or native drug. Unfortunately, monofunctional PEGs, such as monomethoxy-PEG, can carry only one drug molecule per polymer chain, thereby lacking the high drug-carrying capability often sought in delivering bioactive agents.

Thus, there remains a need in the art for improved methods for delivering both hydrophilic and hydrophobic drugs in a therapeutically effective manner. That is to say, there is a need for compositions and methods of drug delivery that are flexible enough to be useful for delivering not only water-insoluble drugs, but are adaptable for use in delivering hydrophilic and charge-bearing bioactive agents as well. The present invention seeks to solve these and other needs in the art.

SUMMARY OF THE INVENTION

The invention provides a unimolecular multi-arm block copolymer comprising a central core molecule providing at least three attachment sites available for covalent attachment, and a copolymer arm covalently attached to each of the attachment sites of the central core molecule. Each copolymer arm comprises an inner polypeptide segment covalently attached to the central core molecule and an outer hydrophilic polymer segment covalently attached to the polypeptide segment. The central core molecule and the polypeptide segments taken together define an inner core region and the hydrophilic polymer segments define a hydrophilic outer region. Biologically active agents can be entrapped within the copolymer structure, preferably within the inner core region of the block copolymer. Depending on the structure and properties of the biologically active agent and the block copolymer, the entrapment can result from various bonding or attraction forces, such as covalent bonding or attraction based on shared hydrophobicity or charge attraction.

The central core molecule is preferably a polyamine. An exemplary polyamine comprises a residue of a polyol core attached through ether linkages to small molecular weight hydrophilic oligomers, such as PEG oligomers, each oligomer having a terminal amine group.

The polypeptide segment preferably comprises hydrophobic amino acid residues, amino acid residues bearing an electric charge, or amino acid residues having pendant functional groups suitable for covalent attachment to drug molecules. Exemplary amino acid residues include residues of glycine, alanine, valine, leucine, isoleucine, methionine, proline, phenylalanine, tryptophan, serine, threonine, asparagine, glutamine, tyrosine, cysteine, lysine, arginine, histidine, aspartic acid, glutamic acid, and combinations thereof.

The hydrophilic polymer segment is preferably a poly(ethylene glycol) ("PEG"), optionally terminated with a capping group, such as alkoxy, or a functional group, such as hydroxyl, active ester, active carbonate, acetal, aldehyde, aldehyde hydrate, alkyl or aryl sulfonate, halide, disulfide, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, or tresylate. The functional group can be used to covalently attach a drug molecule, if desired. In one particular embodiment, the PEG polymer segments bear a targeting moiety that can direct the copolymer to particular sites within the body for targeted release of the physically entrapped drug. Examples of targeting moieties include proteins, antibodies, antibody fragments, peptides, carbohydrates, lipids, oligonucleotides, DNA, RNA, or small molecules having a molecular weight less than 2,000 Daltons.

When a hydrophobic polypeptide segment is employed, the block copolymer forms a unimolecular micelle structure wherein the central core and the polypeptide segment define a hydrophobic core region. By entrapping one or more hydrophobic biologically active agents within this hydrophobic core region, the hydrophobic agent(s) become solubilized. In this way, it is possible to provide a means for administering previously unadministerable agents possessing hydrophobic-limiting solubility. Thus, improved delivery of a hydrophobic agent can be achieved by administering a pharmaceutical composition containing a multi-arm block copolymer of the invention having a drug entrapped within its hydrophobic core region.

The invention further encompasses, among other things, pharmaceutical compositions comprising such block copolymers, methods of making the copolymers, and methods of using the block copolymers as, for example, drug delivery vehicles.

BRIEF DESCRIPTION OF THE DRAWINGS

Figure 1:
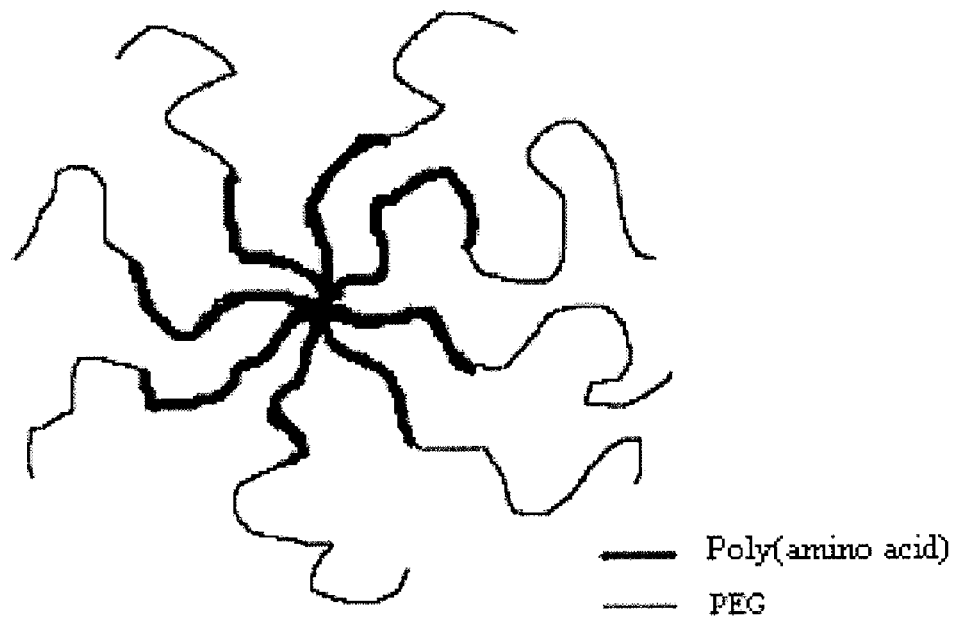
Figure 2:
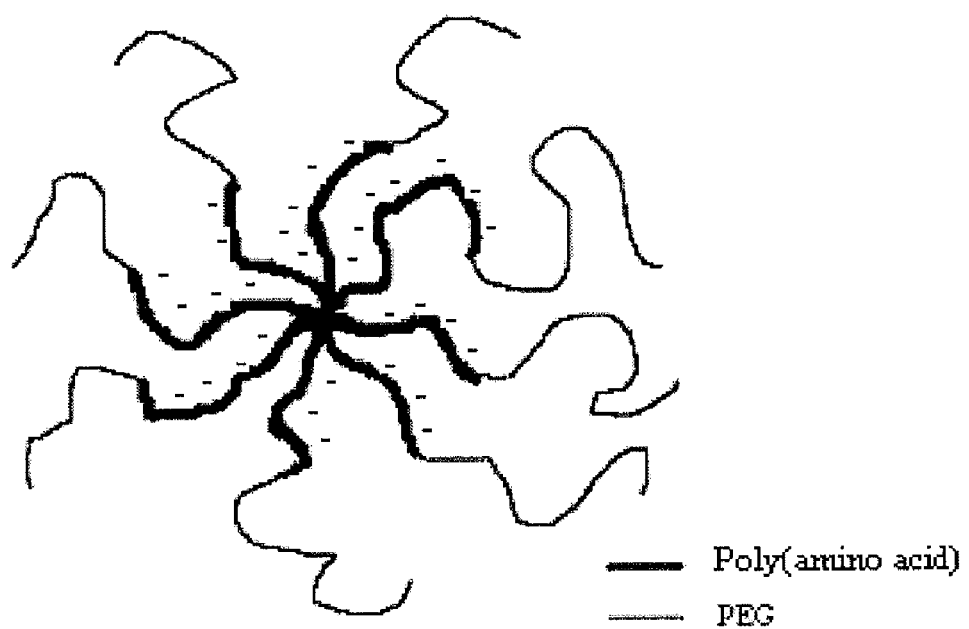
Figure 3:
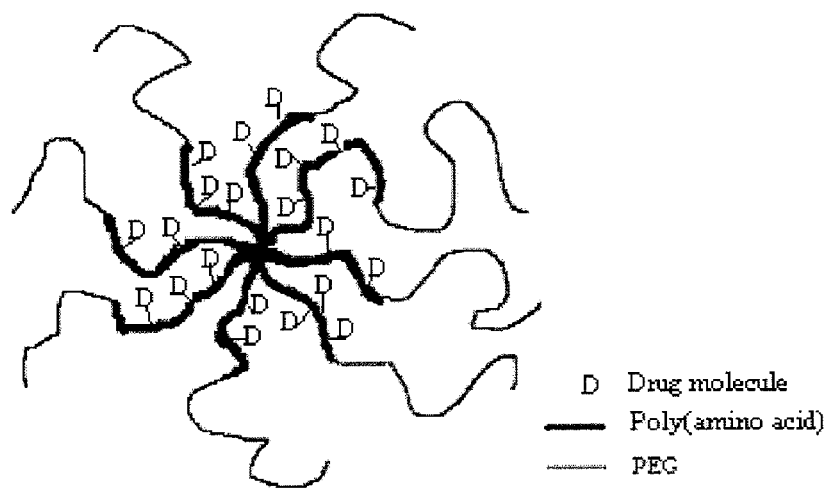
Figure 4:
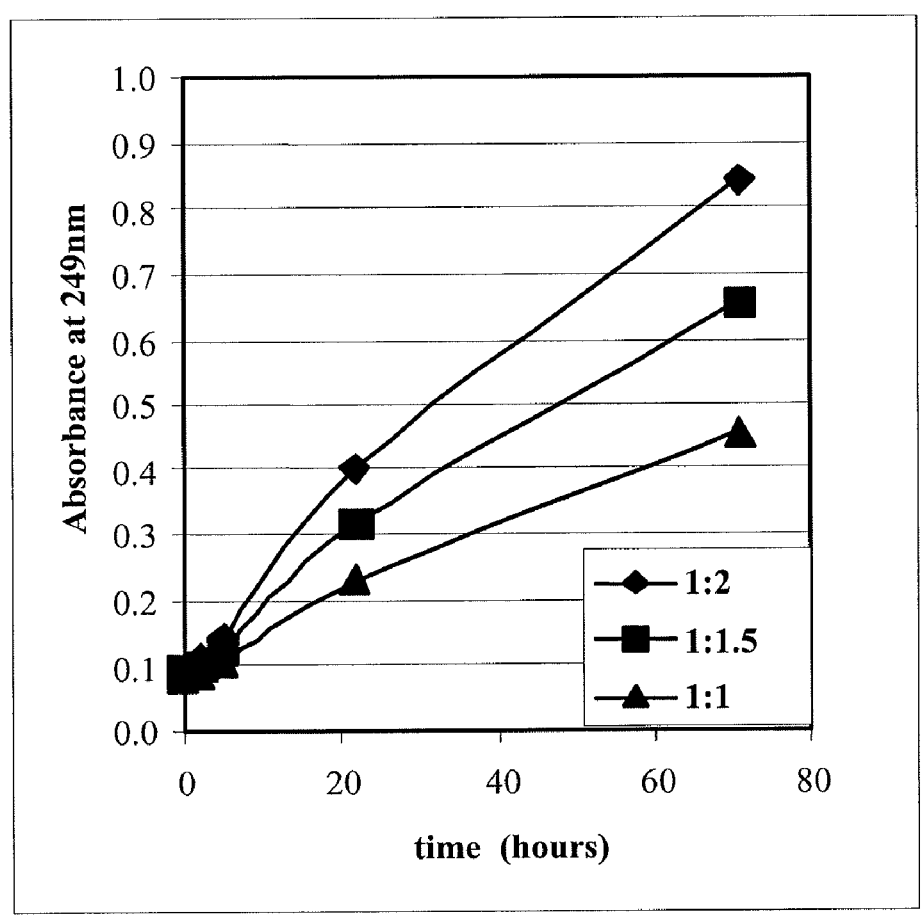

Having thus described the invention in general terms, reference will now be made to the accompanying figures, wherein:

FIG. 1 is an illustration of the general structure of the unimolecular multi-arm block copolymer of the invention;

FIG. 2 is an illustration of the structure of an embodiment of the unimolecular multi-arm block copolymer having a charged inner core region;

FIG. 3 is an illustration of the structure of an embodiment of the unimolecular multi-arm block copolymer having a biologically active agent covalently attached to the polypeptide segment of the copolymer; and FIG. 4 illustrates the change in absorbance over time for several concentrations of cis-diamminodichloro platinum in a solution containing an 8-arm unimolecular block copolymer of the invention.

DETAILED DESCRIPTION OF THE INVENTION

The present invention now will be described more fully. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

It must be noted that, as used in this specification and the claims, the singular forms "a," "an," and "the" include plural referents unless the context clearly dictates otherwise. Thus, for example, reference to "a drug" includes a single drug as well as two or more of the same or different drugs, reference to a "unimolecular multi-arm block copolymer" includes a single unimolecular multi-arm block copolymer as well as two or more of the same of different unimolecular multi-arm block copolymers, reference to an "excipient" includes a single excipient as well as two or more of the same or different excipients, and the like.

The terms "functional group," "active moiety." "activating group," "reactive site," "chemically reactive group," and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react (i.e., "nonreactive" or "inert" groups). For example, as would be understood in the art, the term "active ester" includes those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group. As used herein, the term "functional group" includes protected functional groups.

The term "protected functional group" refers to the presence of a protecting group or moiety that prevents reaction of the chemically reactive functional group under certain reaction conditions. The protecting group will vary depending on the type of chemically reactive group being protected and the reaction conditions employed. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the invention, see for example, Greene, T. W., et al., PROTECTIVE GROUPS IN ORGANIC SYNTHESIS, 3rd ed., John Wiley & Sons, New York, N.Y. (1999).

The terms "linkage" and "linker" are used herein to refer to an atom, group of atoms, or bond(s) that are normally formed as the result of a chemical reaction. A linker of the invention typically links adjacent moieties, such as two polymer segments, via one or more covalent bonds. Hydrolytically stable linkages are linkages that are substantially stable in water and do not react to any significant degree with water at useful pHs, e.g., physiological pH, for an extended period of time, perhaps even indefinitely. A hydrolytically unstable or degradable linkage is a linkage that is degradable in water or in aqueous solutions, including for example, blood, plasma or other physiological fluid. Enzymatically unstable or degradable linkages encompass those linkages that can be degraded by one or more enzymes.

The term "alkyl" refers to hydrocarbon chains typically ranging from about 1 to about 12 carbon atoms in length, preferably from about 1 to about 6 atoms, and includes straight and branched chains. The hydrocarbon chains may be saturated or unsaturated.

"Cycloalkyl" refers to a saturated or unsaturated cyclic hydrocarbon chain, including bridged, fused, or Spiro cyclic compounds, preferably comprising 3 to about 12 carbon atoms, more preferably 3 to about 8.

The term "substituted alkyl" or "substituted cycloalkyl" refers to an alkyl or cycloalkyl group substituted with one or more non-interfering substituents, such as, but not limited to, $C_{3-8}$ cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably $C_{1-6}$ alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more noninterfering groups as substituents. For substitutions on a phenyl ring, the substituents may be in any orientation (i.e., ortho, meta or para).

"Heteroaryl" is an aryl group containing from one to four heteroatoms, preferably sulfur, oxygen, nitrogen, or a combination thereof, which heteroaryl group is optionally substituted at carbon or nitrogen atom(s) with $C_{1-6}$ alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

"Substituted heteroaryl" is heteroaryl having one or more noninterfering groups as substituents.

"Heterocycle" or "heterocyclic" means one or more rings of 5-12 atoms, preferably 5-7 atoms, with or without unsaturation or aromatic character and at least one ring atom that is not carbon. Preferred heteroatoms include sulfur, oxygen, and nitrogen. Multiple rings may be fused, as in quinoline or benzofuran.

"Heteroatom" means any noncarbon atom in a hydrocarbon analog compound. Examples include oxygen, sulfur, nitrogen, phosphorus, arsenic, silicon, selenium, tellurium, tin, and boron.

"Substituted heterocycle" is heterocycle having one or more side chains formed from noninterfering substituents.

"Noninterfering substituents" are those groups that yield stable compounds. Suitable noninterfering substituents or radicals include, but are not limited to, halo, $C_{1-10}$ alkyl, $C_{2-10}$ alkenyl, $C_{2-10}$ alkynyl, $C_{1-10}$ alkoxy, $C_{7-12}$ aralkyl, $C_{7-12}$ alkaryl, $C_{3-10}$ cycloalkyl, $C_{3-10}$ cycloalkenyl, phenyl, substituted phenyl, toluoyl, xylenyl, biphenyl, $C_{2-12}$ alkoxyalkyl, $C_{7-12}$ alkoxyaryl, $C_{7-12}$ aryloxyalkyl, $C_{6-12}$ oxyaryl, $C_{1-6}$ alkylsulfinyl, $C_{1-10}$ alkylsulfonyl, —$(CH_2)_{m''}$—O—$(C_{1-10}$ alkyl) wherein (m") is from 1 to 8, aryl, substituted aryl, substituted alkoxy, fluoroalkyl, heterocyclic radical, substituted heterocyclic radical, nitroalkyl, —$NO_2$, —CN, —NRC (O)—$(C_{1-10}$ alkyl), —C(O)—$(C_{1-10}$ alkyl), $C_{2-10}$ thioalkyl, —C(O)O—$(C_{1-10}$ alkyl), —OH, —$SO_2$, =S, —COOH, —NR, carbonyl, —C(O)—$(C_{1-10}$ alkyl)-$CF_3$, —C(O)—$CF_3$, —C(O)$NR_2$, —$(C_{1-10}$ alkyl)-S—$(C_{6-12}$ aryl), —C(O)—$(C_{6-12}$ aryl), —$(CH_2)_{m''}$—O—$(CH_2)_{m''}$—O—$(C_{1-10}$ alkyl) wherein each (m") is independently selected from 1 to 8, —C(O)NR, —C(S)NR, —$SO_2$NR, —NRC(O)NR, —NRC (S)NR, salts thereof, and the like. Each R as used herein is independently selected from the group consisting of H, unsubstituted alkyl, substituted alkyl, unsubstituted aryl, substituted aryl, aralkyl, and alkaryl.

The terms "drug," "biologically active molecule," "biologically active moiety," "biologically active agent," "active agent," and the like are used interchangeably herein and mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs (e.g., nonpeptidic drugs), dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "nonpeptidic" refers to a structure substantially free of amino acids connected via peptide linkages. Thus, for example, when nonpeptidic is used in reference to a polymer backbone, the polymer backbone is substantially free of amino acids connected via peptide linkages. The polymer backbone may, however, include a minor number of peptide linkages spaced along the length of the backbone, such as, for example, no more than about 1 peptide linkage per about 50 monomer units.

"Polypeptide" or "poly(amino acid)" refers to any molecule comprising a series of amino acid residues linked through amide linkages along the alpha carbon backbone. Modifications of the peptide side chains may be present, along with glycosylations, hydroxylations, and the like. Additionally, other nonpeptidic molecules, including lipids and small drug molecules, may be attached to the polypeptide. The polypeptide may comprise any combination or sequence of amino acid residues.

"Amino acid" refers to organic acids containing both a basic amine group and an acidic carboxyl group. The term encompasses essential and nonessential amino acids and both naturally occurring and synthetic or modified amino acids. The most common amino acids are listed herein by either their full name or by the three letter or single letter abbreviations: Glycine (Gly, G); Alanine (Ala, A); Valine (Val, V); Leucine (Leu, L); Isoleucine (Ile, I); Methionine (Met, M); Proline (Pro, P); Phenylalanine (Phe, F); Tryptophan (Trp, W); Serine (Ser, S); Threonine (Thr, T); Asparagine (Asn, N); Glutamine (Gln, Q); Tyrosine, (Tyr, Y); Cysteine (Cys, C);

Lysine (Lys, K); Arginine (Arg, R); Histidine (His, H); Aspartic Acid (Asp, D); and Glutamic acid (Glu, E). Reference to an amino acid is without regard to absolute configuration and the description includes amino acids in either the L or D form.

By "residue" is meant the portion of a molecule remaining after reaction with one or more molecules. For example, an amino acid residue in a polypeptide chain is the portion of an amino acid remaining after forming peptide linkages with adjacent amino acid residues.

"Hydrophobic" refers to molecules having a greater solubility in octanol than in water, typically having a much greater solubility in octanol. Conversely, "hydrophilic" refers to molecules having a greater solubility in water than in octanol.

"Oligomer" refers to short monomer chains comprising 2 to about 20 monomer units, preferably 2 to about 10 monomer units.

"Unimolecular" means the entire molecule is covalently bonded together in a single molecular structure, rather than reliant on other noncovalent bonding or attraction forces as in a traditional micelle.

The term "patient," refers to a living organism suffering from or prone to a condition that can be prevented or treated by administration of a drug, and includes both humans an animals.

"Optional" or "optionally" means that the subsequently described circumstance may or may not occur, so that the description includes instances where the circumstance occurs and instances where it does not.

II. The Unimolecular Multi-Arm Block Copolymer

The present invention provides a unimolecular multi-arm block copolymer having an inner core region defined by a central core molecule having polypeptide segments covalently attached thereto and an outer hydrophilic region defined by hydrophilic polymer segments covalently attached to each of the polypeptide polymer segments. Thus, each arm of the multi-arm structure is a block copolymer comprising an inner (i.e. closer or proximal to the central core molecule) polypeptide polymer segment and an outer (i.e. further or distal from the central core molecule) hydrophilic polymer segment.

The unimolecular multi-arm block copolymers of the invention are particularly well suited for encapsulation or entrapment of biologically active molecules within the inner core region. As used herein, "encapsulation" or "entrapment" is intended to refer to the physical confinement of a drug molecule within the inner core region of the copolymer, whether by covalent attachment, charge interaction, metal-acid complex, van der Waals forces, or other attraction or bonding force.

The unimolecular multi-arm block copolymer typically has a total number average molecular weight of from about 5,000 Da to about 120,000 Da, preferably from about 10,000 Da to about 100,000 Da, and more preferably from about 20,000 Da to about 80,000 Da. An illustration of the general structure of the block copolymer of the invention is shown in FIG. 1.

The outer hydrophilic polymer segments are preferably poly(ethylene glycol), although other hydrophilic polymer segments can also be used. In certain embodiments, a targeting moiety that can direct the copolymer structure to particular sites within the body is attached to one or more of the hydrophilic polymer segments for targeted release of an entrapped drug.

The use of a polypeptide polymer segment as part of the inner core region of the unimolecular multi-arm structure provides tremendous flexibility in designing and adjusting the drug delivery properties of the multi-arm structure. Interaction between a drug and the core region of the unimolecular multi-arm structure can greatly affect drug loading and drug release characteristics. In the present invention, depending on the structure of the polypeptide polymer segments, the inner core region of the unimolecular multi-arm structure can be hydrophobic, charged, suitable for covalent attachment to drug molecules, or any combination thereof.

Hydrophobic Core Region

Polypeptides can exhibit a broad range of hydrophobicity. When a hydrophobic polypeptide is utilized, it is believed that the multi-arm block copolymer acts as a unimolecular micelle in aqueous solution, the micelle structure comprising a central hydrophobic core region bounded by a hydrophilic outer region. As a result, in this embodiment, the multi-arm block copolymers of the invention are capable of increasing the aqueous solubility of hydrophobic biologically active agents by encapsulating or physically entrapping them within the hydrophobic core region of the multi-arm block copolymer structure. The exact structure of the polypeptide, and consequently the hydrophobicity thereof, can be adjusted as necessary to maximize affinity for a particular drug molecule.

Compared to conventional linear micelle structures, the unimolecular nature of the multi-arm block copolymers of the invention results in less sensitivity to concentration, such that the block copolymers of the invention are less likely to release the entrapped drug molecules at an undesirably rapid rate. The multi-arm block copolymers of the invention are covalently bound molecular units rather than aggregates of individual molecules. As a result, unintended disassembly of the structure in vivo due to insufficient concentrations of the micelle-forming materials is avoided with the presently described multi-arm block copolymers. Intentional disassembly of the multi-arm block copolymers, however, can occur in vivo by including one or more hydrolytically unstable linkages within the polymer segments. In contrast to the spontaneous concentration-dependent disassembly associated with aggregates of molecules, the multi-arm block copolymers of the invention having one or more hydrolytically unstable linkages advantageously disassemble over time in a predictable manner based on the rate of hydrolysis. Further, since chemical modification of the active agent is not required to obtain an increase in solubility, the possibility of the copolymer reducing efficacy of the entrapped drug is greatly reduced.

Although not wishing to be bound by any particular theory, it is believed that the level of hydrophobicity and size of the hydrophobic polypeptide affect the drug loading and drug release characteristics of the multi-arm block copolymer. In general, it is believed that larger hydrophobic polypeptide segments and hydrophobic polypeptide segments formed from amino acids having relatively greater degrees of hydrophobicity will result in higher drug loading and slower drug release profiles in solution. Conversely, smaller hydrophobic polypeptide segments and hydrophobic polypeptide segments formed from amino acids having relatively lower degrees of hydrophobicity will result in reduced drug loading and more rapid drug release. Using routine experimentation, one of ordinary skill in the art can determine an appropriate polypeptide segment composition and size for any given drug. For example, a series of drug-containing multi-arm block copolymers can be prepared as discussed herein, each having a difference size of polypeptide segment. The multi-arm block copolymer having the greatest efficacy upon administration to a patient has an appropriately sized polypeptide segment. A similar approach can be used to determine an appropriate polypeptide segment content (i.e., the amino acid residues present in the polypeptide segment).

Here, however, a series of drug-containing multi-arm block copolymers having different amino acid residues in the polypeptide segment are tested.

Charged Core Region

In another embodiment, hydrophilic biologically active agents that bear a charge in aqueous media can be entrapped within the inner core region of the unimolecular multi-arm block copolymers of the invention by selecting a polypeptide segment having an opposite charge. The opposite charges result in attraction between the core region of the multi-arm structure and the drug. For example, if an inner core region with a positive charge is needed to entrap a negatively charge active agent, a polypeptide segment can be formed from amino acid residues that are positively charged, preferably at or near physiological pH (i.e., pH of about 7.4). Lysine (having a pK of about 10.0) and arginine (having a pK of about 12.0) are positively charged at or near physiological pH. Other amino acids can also be positively charged, depending on the pH of the environment. For example, the imidazole ring of histidine can be positively charged.

If an inner core region with a negative charge is desired for an active agent bearing a positive charge, a polypeptide segment can be faulted from amino acid residues that are preferably negatively charged, preferably at or near physiological pH (i.e., pH of about 7.4). Glutamic acid and aspartic acid (both having a pK of about 4.4) are negatively charged at or near physiological pH. Depending on the pH of the environment, other amino acids such as cysteine can also be used to provide a negative charge.

The use of charge attraction to entrap a biologically active molecule is particularly advantageous for entrapping DNA, RNA or oligonucleotides. The entrapped drug is released in a sustained and extended manner from the charged inner core region. An illustration of a charged-core embodiment of the block copolymer of the invention is shown in FIG. 2. Areas of the polypeptide segment wherein an amino acid residues bears a negative charge are depicted with a negative ("−") sign.

Core Regions Suitable for Covalent Attachment to Drugs

In yet another embodiment, the biologically active agent can be covalently attached to the inner core region of the multi-arm block copolymer of the invention by covalently attaching the biologically active agent to a pendant functional group spaced within the polypeptide chain. For example, polypeptides formed from a number of different amino acids, such as aspartic acid and glutamic acid, include pendant carboxylic acid groups on their side chains. These acid groups can readily react with, for example, a biologically active agent bearing an amine group, thereby linking the biologically active agent to the polypeptide chain via an amide linkage. In addition, a polypeptide segment comprising an amine-containing lysine residue can react with a biologically active agent bearing a carboxylic acid group, thereby forming an amide linkage. An illustration of covalent attachment of drug molecules to the block copolymer of the invention is shown in FIG. 3.

If desired, the linkage between the polypeptide and the biologically active agent can be a degradable linkage, such as an ester linkage, carbonate linkage, imine linkage, hydrazone linkage, acetal linkage, or ortho ester linkage. In this manner, the block copolymer can act essentially as a prodrug, releasing the drug molecules upon hydrolysis of the degradable linkages in solution.

In any of the above embodiments, as compared to linear block copolymers, the multi-arm block copolymers of the invention can better protect the drug molecules from enzymatic degradation by sheltering the drug within the inner core region. Also, in embodiments incorporating a targeting moiety, the targeting moiety can be used more efficiently as compared to linear block copolymers. In the present case, a targeting moiety attached to only a few copolymer arms can effectively deliver a number of drug molecules entrapped within the core region of the multi-arm structure, thereby increasing the delivered drug "payload" relative to a targeted linear polymer having only one or two drug moieties covalently attached thereto.

It is believed that the number of arms of the multi-arm block polymer has an impact on the drug loading and drug release characteristics of the copolymer embodiments having a hydrophobic or charged core region. Generally, the presence of fewer copolymer arms results in reduced drug loading and more rapid drug release. The use of a copolymer with a very large number of arms can also reduce drug loading because of the substantial increase in density and concomitant reduction in interstitial space within the core region of the copolymer structure. Copolymers with a higher number of arms are, however, less likely to have drug release characteristics that depend on concentration. In light of the foregoing, an optimal range for the number of arms of the block copolymer can be determined such that both desirable drug loading and drug release characteristics are obtained for any particular hydrophobic drug. One of ordinary skill in the art can determine through routine experimentation what number of arms is appropriate in any given context. For example, one of ordinary skill in the art can create a series of differently numbered arms of drug-containing multi-arm block copolymers, monitor the efficacy of each copolymer in the series upon injection into a patient, and subsequently identify the appropriate number of arms as being associated with the number of arms in the copolymer having the best efficacy. In most embodiments, however, the number of arms is in the range of from 3 to about 25, and can therefore be 3, 4, 5, 6, 7, 8, 9, 10, 11, 12, 13, 14, 15, 16, 17, 18, 19, 20, 21, 22, 23, 24, or 25. It is preferred, however, that the number of arms in the multi-arm block copolymers described herein is at least 5, more preferably at least about 8, and most preferably at least about 10.

The polypeptide and hydrophilic polymer segments are preferably not "hyper-branched" or dendritic in nature, such as the dendrimers described in U.S. Pat. No. 5,830,986, wherein branched compounds are attached in numerous successive layers to a central core. Instead, both polymer segments are preferably substantially linear in nature as depicted in FIG. 1. However, some branching in either polymer segment may be present. For example, a branched poly(ethylene glycol) polymer comprising two polymer backbones attached to lysine linker can be used as the hydrophilic polymer.

Although the specific examples of multi-arm block copolymers in the appended experimental section utilize the same block copolymer structure for each copolymer arm, it is possible to utilize different copolymer structures within the same multi-arm structure. In other words, the present invention includes embodiments wherein more than one polypeptide/hydrophilic polymer combination is attached to the same core molecule.

A. The Central Core

The central core molecule is derived from a molecule that provides a number of polymer attachment sites equal to the number of desired copolymer arms. By "attachment site" is meant a functional group capable of reacting with another molecule, such as an amino acid, to form a covalent linkage. Preferably, the central core molecule is a residue of a polyamine having at least three termini bearing an amine group. By "polyamine" is meant a branched molecule containing a plurality of terminal amine groups available as attachment sites for attaching the copolymer arms to the core molecule. The use of a polyamine core is preferred because the amine groups of the core readily react with the carboxylic acid group of an amino acid to form an amide linkage. Core molecules having other functional groups available for attachment to the copolymer arms can, however, also be used.

In embodiments utilizing a polyamine core, the number of amine groups will dictate the number of copolymer arms in the multi-arm structure. Preferably, the polyamine comprises from 3 to about 25 amine groups. In various embodiments, the polyamine comprises at least about 5 amine groups, at least about 8 amine groups, or at least about 10 amine groups.

The core molecule typically has a total number average molecule weight of from about 250 Da to about 15,000 Da, preferably from about 500 Da to about 10,000 Da, and more preferably from about 1,000 Da to about 5,000 Da. Thus, exemplary total number average molecular weights of the core molecule include the following: about 250 Da; about 300 Da; about 350 Da; about 400 Da; about 450 Da; about 500 Da; about 550 Da; about 600 Da; about 650 Da; about 700 Da; about 750 Da; about 800 Da; about 850 Da; about 900 Da; about 950 Da; about 1,000 Da; about 1,500 Da; about 2,000 Da; about 2,500 Da; about 3,000 Da; about 3,500 Da; about 4,000 Da; about 4,500 Da; about 5,000 Da; about 5,500 Da; about 6,000 Da; about 6,500 Da; about 7,000 Da; about 7,500 Da; about 8,000 Da; about 8,500 Da; about 9,000 Da; about 9,500 Da; about 10,000 Da; about 10,500 Da; about 11,000 Da; about 11,500 Da; about 12,000 Da; about 12,500 Da; about 13,000 Da; about 13,500 Da; about 14,000 Da; about 14,500 Da; and about 15,000 Da. In the embodiments exemplified in the appended experimental section, the molecular weight of the polyamine core molecule is about 2,000 Da.

In a preferred embodiment, the polyamine core molecule is formed by covalent attachment of small molecular weight hydrophilic oligomers bearing an amine group to a polyol core. In this embodiment, the central core molecule comprises the residue of a polyol having at least three hydroxyl groups available for polymer attachment. A "polyol" is a molecule comprising a plurality of available hydroxyl groups. Depending on the desired number of copolymer arms, the polyol will typically comprise from about 3 to about 25 hydroxyl groups, preferably at least 5, more preferably at least about 8, and most preferably at least about 10. The polyol may include other protected or unprotected functional groups as well without departing from the invention. Although the spacing between hydroxyl groups will vary from polyol to polyol, there are typically about 1 to about 20 atoms, such as carbon atoms, between each hydroxyl group, preferably 1 to about 5. Preferred polyols include glycerol, reducing sugars such as sorbitol, pentaerythritol, and glycerol oligomers, such as hexaglycerol. For example, a cyclodextrin such as hydroxypropyl-β-cyclodextrin, which has 21 available hydroxyl groups, can form a 21-arm block copolymer. The particular polyol chosen will depend on the desired number of copolymer arms in the multi-arm copolymer structure wherein the number of hydroxyl groups in the polyol will correspond to the total number of copolymer arms.

When covalently attaching small molecular weight hydrophilic oligomers to a core molecule, each hydrophilic oligomer should have a molecular weight sufficiently small to avoid significantly affecting the level of hydrophobicity of the inner core region of the multi-arm structure. Typically, an ethylene glycol oligomer chain having a molecular weight from about 88 Da to about 1,000 Da, preferably from about 100 Da to about 1,000 Da, more preferably from about 100 Da to about 500 Da is used. In one embodiment, the ethylene glycol oligomer has a number average molecular weight of about 200 to about 300 Da.

The oligomer segments can be readily attached to the polyol core by using an oligomer having a functional group suitable for reaction with the available hydroxyl groups of the polyol. For example, a bifunctional ethylene glycol oligomer having a mesylate group at one terminus and an amine group at the other terminus can be reacted with a polyol to form an ester linkage between the ethylene glycol oligomer and the polyol. The amine groups of the ethylene glycol oligomer would then be available for reaction with an amino acid to form the polypeptide segment of the copolymer arms. Alternatively, the ethylene glycol oligomer can be directly polymerized onto the polyol core as described in, for example, U.S. Pat. No. 6,046,305, followed by derivatizing the terminal group of the PEG oligomer to form an amine group.

The general structure of a preferred polyamine central core molecule is shown below.

   Formula I wherein:

A' is a residue of a polyol, such as glycerol, sorbitol, pentaerythritol, glycerol oligomers, or a polyol-containing cyclodextrin, e.g., hydroxypropyl-β-cyclodextrin;

$PEG_o$ is a PEG oligomer having a molecular weight of about 100 Da to about 1,000 Da; and (n) is 3 to about 25, and is used to represent the number of ($-O-PEG_o-NH_2$) moieties attached to the central core molecule.

Polyamine structures in accordance with Formula I are prepared from commercially available multi-arm ethylene glycols available from NOF Corporation (Tokyo, Japan) or can be readily prepared using commercially available reagents as described above.

Also suitable for use as the central core are branched polyamines such as those described above but absent an ethylene glycol component.

B. The Polypeptide Segment

The polypeptide should be generally nontoxic and biocompatible, meaning that the benefits derived from its proposed use in connection with living tissues (e.g., administration to a patient) outweighs any deleterious effects as evaluated by a clinician, e.g., a physician. In preferred embodiments, the polypeptide segments comprise residues of amino acids such as glycine, alanine, valine, leucine, isoleucine, methionine, proline, phenylalanine, tryptophan, serine, threonine, asparagine, glutamine, tyrosine, cysteine, lysine, arginine, histidine, aspartic acid, glutamic acid, or combinations thereof. Particularly preferred amino acids that enhance the hydrophobic nature of the polypeptide segment are selected from the group consisting of valine, leucine, isoleucine, phenylalanine, tryptophan, tyrosine, methionine, and cysteine. If a charged inner core region is desired, the polypeptide preferably comprises residues of charged or chargeable amino acids, such as arginine, lysine, histidine, glutamic acid, aspartic acid, or combinations thereof.

The polypeptide segment of the block copolymer will typically have a number average molecular weight of about 100 Da to about 20,000 Da, preferably about 500 Da to about 10,000 Da. For example, polypeptide segments having a molecular weight of about 100 Da, about 200 Da, about 300 Da, about 500 Da, about 800 Da, about 1,000 Da, about 2,000 Da, about 3,000 Da, about 4,000 Da, and about 5,000 Da are useful in the present invention.

When a polyamine core is utilized, the polypeptide segment is typically attached to the central core molecule by amide linkages. The polypeptide is also preferably attached to the hydrophilic polymer segment by an amide linkage. In preferred embodiments, the polypeptide segment has the following structure:

$$(-C(O)-CHR-NH-)_m \quad \text{Formula II}$$

wherein:

R is hydrogen, alkyl (e.g., $C_{1-6}$ alkyl) wherein one or more carbon atoms of the alkyl chain can be optionally replaced with a heteroatom (e.g., O, S or N), or substituted alkyl; and (m) is about 3 to about 100, preferably about 3 to about 50, and more preferably about 3 to about 30.

Preferred substituents for the R alkyl chain include aryl, substituted aryl, heteroaryl, substituted heteroaryl, and functional groups, such as thiol, amine, carboxylic acid, esters of carboxylic acid, and the like. As noted above, pendant functional groups spaced along the polypeptide backbone can be used to covalently attach biologically active agents to the polypeptide segment. Exemplary functional groups include hydroxyl, active ester (e.g. N-hydroxysuccinimidyl ester or 1-benzotriazolyl ester), active carbonate (e.g. N-hydroxysuccinimidyl carbonate and 1-benzotriazolyl carbonate), acetal, aldehyde, aldehyde hydrate, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, or tresylate.

The polypeptide segment will typically be enzymatically degradable. The use of a degradable polypeptide allows the multi-arm block copolymer to degrade in vivo over time, thus increasing renal clearance of the copolymer. In addition, the degradation of the polypeptide provides an additional feature of these polymers, i.e., the ability to control the rate of release of the entrapped drug.

C. The Hydrophilic Polymer

The hydrophilic polymer segment can comprise any hydrophilic polymer and the invention is not limited in this regard. As with the polypeptide, the hydrophilic polymer should generally be nontoxic and biocompatible. Preferably, poly(ethylene glycol) ("PEG") is used as the hydrophilic polymer segment. The term PEG includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In its simplest form, PEG has the formula $$-CH_2CH_2O-(CH_2CH_2O)_{n''}-CH_2CH_2- \quad \text{Formula III}$$

wherein (n") is from about 2 to about 4,000, typically about 10 to about 4,000, and more typically from about 20 to about 500.

Although the number average molecular weight of the PEG polymer backbone can vary, PEGs having a number average molecular weight of from about 100 Da to about 20,000 Da, preferably about 500 Da to about 10,000 Da, are particularly useful as the hydrophilic polymer segment. For example, PEG polymer segments having a molecular weight of about 100 Da, about 200 Da, about 300 Da, about 500 Da, about 800 Da, about 1,000 Da, about 2,000 Da, about 3,000 Da, about 4,000 Da, about 5,000 Da, about 6,000 Da, about 7,000 Da, about 8,000 Da, about 9,000 Da, about 10,000 Da, about 11,000 Da, about 12,000 Da, about 13,000 Da, about 14,000 Da, about 15,000 Da, about 16,000 Da, about 17,000 Da, about 18,000 Da, about 19,000 Da, and about 20,000 Da are useful in the present invention.

In one form useful in the present invention, free or non-bound PEG is a linear polymer terminated at each end with hydroxyl groups:

$$HO-CH_2CH_2O-(CH_2CH_2O)_{n''}-CH_2CH_2-OH \quad \text{Formula IV}$$

wherein the definition of (n") is the same as that provided with respect to Formula III.

The above polymer, alpha-,omega-dihydroxylpoly(ethylene glycol), can be represented in brief form as HO-PEG-OH where it is understood that the -PEG- symbol represents a structure of Formula III above.

Another type of PEG useful in the present invention is methoxy-PEG-OH, or mPEG in brief, in which one terminus is the relatively inert methoxy group, while the other terminus is a hydroxyl group that is subject to ready chemical modification. The structure of mPEG is given below.

$$CH_3O-CH_2CH_2O(CH_2CH_2O)_{n''}-CH_2CH_2-OH \quad \text{Formula V}$$

wherein the definition of (n") is the same as that provided with respect to Formula III.

Multi-armed or branched PEG molecules, such as those described in U.S. Pat. No. 5,932,462, which is incorporated by reference herein in its entirety, can also be used as the PEG polymer. For example, the hydrophilic PEG segment can have the structure:

$$\begin{array}{c} poly_a - P \\ | \\ R'' - C - \\ | \\ poly_b - Q \end{array} \quad \text{Formula VI}$$

wherein:

$poly_a$ and $poly_b$ are PEG backbones, such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

The PEG polymer may alternatively comprise a forked PEG. An example of a forked PEG is represented by PEG-YCHZ$_2$, where Y is a linking group and Z is an activated terminal group, linked to CH by a chain of atoms of defined length. International Application No. PCT/US99/05333, the contents of which are incorporated by reference herein, discloses various forked PEG structures capable of use in the present invention. The chain of atoms linking the Z functional groups to the branching carbon atom serve as a tethering group and may comprise, for example, an alkyl chain, ether linkage, ester linkage, amide linkage, or a combination thereof.

The PEG polymer may comprise a pendant PEG molecule having reactive groups, such as carboxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more weak or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

-PEG-CO$_2$-PEG-+H$_2$O→-PEG-CO$_2$H+HO-PEG-

Other hydrolytically degradable linkages, useful as a degradable linkage within a polymer backbone, include carbonate linkages; imine linkages resulting, for example, from reaction of an amine and an aldehyde (see, e.g., Ouchi et al. (1997) *Polymer Preprints* 38(1):582-3, which is incorporated herein by reference.); phosphate ester linkages formed, for example, by reacting an alcohol with a phosphate group; hydrazone linkages which are typically formed by reaction between a hydrazide and an aldehyde; acetal linkages that are typically formed by reaction between an aldehyde and an alcohol; ortho ester linkages that are formed, for example, by reaction between a formate and an alcohol; and oligonucleotide linkages formed, for example, by reaction between a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

Many other polymers are also suitable for the invention. Polymer backbones that are nonpeptidic and water-soluble, with from 2 to about 300 termini, are particularly useful in the invention. Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. These polymers may be linear, or may be in any of the above-described forms (e.g., branched, forked, and the like).

Those of ordinary skill in the art will recognize that the foregoing list of hydrophilic polymer backbones is by no means exhaustive and is merely illustrative, and that all polymeric materials having the qualities described above are contemplated.

A targeting moiety or drug molecule can optionally be covalently attached to the hydrophilic polymer segment. As used herein, "targeting moiety" includes any chemical moiety capable of binding to, or otherwise exhibiting an affinity for, a particular receptor, ligand, type of tissue, or component of any of the foregoing. The addition of a targeting moiety to the copolymer structure can direct the copolymer to particular sites within the body for targeted release of the physically entrapped drug. For example, certain moieties are known to exhibit an affinity for hydroxyapatite surfaces (i.e., calcium phosphate), such as bone. Exemplary hydroxyapatite-targeting moieties include tetracycline, calcein, bisphosphonates, such as 4-amino-1-hydroxybutane-1,1-diphosphonic acid, ditetrabutylammonium salt (AHBDP) or derivatives thereof, polyaspartic acid, polyglutamic acid, and aminophosphosugars. Additional targeting moieties include proteins, antibodies, antibody fragments, peptides, carbohydrates, lipids, oligonucleotides, DNA, RNA, or small molecules having a molecular weight less than 2,000 Da. In a preferred embodiment, the targeting moiety is mono-folic acid or anti-EGFr Fab. Folic acid is especially preferred for targeted delivery of anticancer agents via attachment to the multi-arm copolymer delivery vehicles as described herein. Folic acid, as a targeting agent, is useful for targeting tumors that overexpress folate receptors. Exemplary tumors falling into this category include ovarian carcinomas, and solid tumors such as head and neck tumors, lung cancers and colorectal cancers. Thus, the multi-arm block copolymers of the invention, when attached to folic acid, are particularly preferred for delivery of anticancer agents useful in the prevention or treatment of any of the aforementioned cancers.

The PEG polymer segment may further include one or more capping groups or functional groups covalently attached to the PEG molecule, such as at a terminus of the PEG segment distal from the point of attachment to the polypeptide. The capping group is typically a relatively inert group, such as an alkoxy group (e.g. methoxy or ethoxy) or benzyloxy. In one embodiment, one or more of the PEG polymer segments bear a functional group capable of reacting with a targeting moiety or drug molecule so that such molecules can be attached to the PEG polymer. Exemplary functional groups include hydroxyl, active ester (e.g. N-hydroxysuccinimidyl ester or 1-benzotriazolyl ester), active carbonate (e.g. N-hydroxysuccinimidyl carbonate and 1-benzotriazolyl carbonate), acetal (as used herein, the term "acetal" encompasses ketals as well), aldehyde, aldehyde hydrate, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate, and tresylate.

Specific examples of terminal functional groups for the polymer backbones of the invention include: N-succinimidyl carbonate (see e.g., U.S. Pat. Nos. 5,281,698, and 5,468,478); amine (see, e.g., Buckmann et al. (1981) *Makromol. Chem.* 182:1379, and Zalipsky et al. (1983) *Eur. Polym. J.* 19:1177); hydrazide (see, e.g., Andresz et al. (1978) *Makromol. Chem.* 179:301); succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997, and U.S. Pat. No. 5,672,662); succinimidyl succinate (see, e.g., Abuchowski et al. (1984) *Cancer Biochem. Biophys.* 7:175, and Joppich et al. (1979) *Makromol. Chem.* 180:1381); succinimidyl ester (see, e.g., U.S. Pat. No. 4,670,417); benzotriazole carbonate (see, e.g., U.S. Pat. No. 5,650,234); glycidyl ether (see, e.g., Pitha et al. (1979) *Eur. J. Biochem.* 94:11, and Elling et al. (1991) *Biotech. Appl. Biochem.* 13:354); oxycarbonylimidazole (see, e.g., Beauchamp et al. (1983) *Anal. Biochem.* 131:25, and Tondelli et al. (1985) *J. Controlled Release* 1:251); p-nitrophenyl carbonate (see, e.g., Veronese et al. (1985) *Appl. Biochem. Biotech.* 11:141, and Sartore et al. (1991) *Appl. Biochem. Biotech.* 27:45); aldehyde (see, e.g., Harris et al. (1984) *J. Polym. Sci. Chem. Ed.* 22:341, and U.S. Pat. Nos. 5,824,784, and 5,252,714); maleimide (see, e.g., Goodson et al. (1990) *Bio/Technology* 8:343, Romani et al. (1984) *Chemistry of Peptides and Proteins* 2:29), and Kogan (1992) *Synthetic Comm.* 22:2417); orthopyridyl-disulfide (see, e.g., Woghiren et al. (1993) *Bioconj. Chem.* 4:314); acrylol (see, e.g., Sawhney et al. (1993) *Macromolecules* 26:581); and vinylsulfone (see, e.g., U.S. Pat. No. 5,900,461). All of the above references are incorporated herein by reference.

Exemplary Unimolecular Multi-Arm Block Copolymer Structures

More specific structural embodiments of the block copolymers of the invention will now be described. The specific structures shown below are presented as exemplary structures only, and are not intended to limit the scope of the invention.

In one embodiment, the block copolymer of the invention has the structure:

$$A(-O-B-L_1-C)_m-(L_2-D-E)_{n'} \quad \text{Formula VII}$$

wherein:

A is a central core molecule comprising a residue of a polyol, such as glycerol, sorbitol, pentaerythritol, glycerol oligomers, or polyol-containing cylodextrin such as hydroxypropyl-β-cyclodextrin;

O is oxygen;

B is a hydrophilic oligomer, such as a PEG oligomer;

C is a polypeptide segment;

D is a hydrophilic polymer segment, such as a PEG polymer;

E is a capping group (e.g., alkoxy) or a functional group (e.g., hydroxy, active esters, and so forth);

$L_1$ and $L_2$ are linkages, such as amide linkages;

(m') is 3 to about 25 and is used to represent the number of (—O—B-$L_1$-C) moieties attached to central core molecule;

(n') is 2 to about 25 and is used to represent the number of ($L_2$-D-E) moieties attached to the (m') number of (—O—B-$L_1$-C) moieties, each (—O—B-$L_1$-C) moiety bearing a single ($L_2$-D-E) moiety; and (n')≦(m').

A preferred embodiment comprising a targeting moiety has the structure:

(T-D-$L_2$-C-$L_1$-B—O—)$_p$A(-O—B-$L_1$-C-$L_2$-D-E)$_k$      Formula VIII wherein:

each A, O, B, C, D, E, $L_1$ and $L_2$ is independently as described above with respect to Formula VII;

T is a targeting moiety;

(p) is a positive integer of at least 1 or greater and represents the number of (T-D-$L_2$-C-$L_1$-B—O—) moieties attached to the central core molecule;

(k) is a positive integer of at least 1 or greater and represents the number of (—O—B-$L_1$-C-$L_2$-D-E) moieties attached to the central core molecule; and the sum of (k) and (p) is from 3 to about 25. In one embodiment, (p) is 1 to about 5, preferably 1 to about 3, and the sum of (k) and (p) is about 6 to about 21, preferably about 8 to about 15.

Formula IX below is an exemplary unimolecular 8-arm polypeptide-PEG block copolymer made in accordance with the invention.

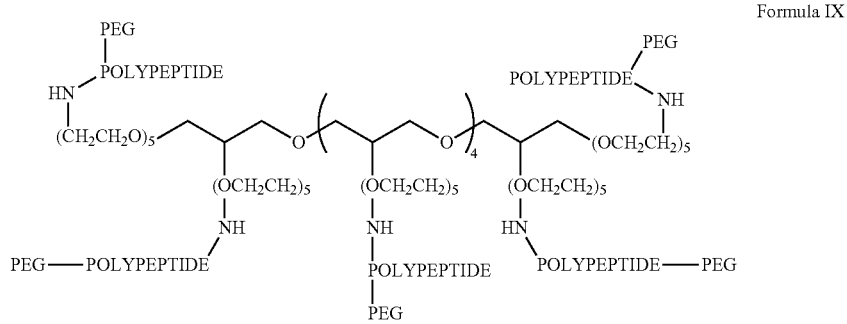

Formula IX wherein:

each POLYPEPTIDE is a polypeptide segment, preferably a polypeptide formed from residues of aspartic acid, glutamic acid or lysine; and each PEG is poly(ethylene glycol), preferably including a terminal capping or functional group as described above.

Particularly preferred structures for POLYPEPTIDE in Formula IX are shown below:

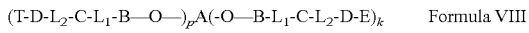

poly(aspartic acid)

poly(glutamic acid)

poly(lysine)

wherein (m) is as defined above with respect to Formula II.

E. The Biologically Active Agent

The biologically active moiety or drug that is carried within the unimolecular multi-aim block copolymer of the invention may be any biologically active agent capable of being physically entrapped within the block copolymer structure. The entrapped or encapsulated drug may be utilized per se or in the form of a pharmaceutically acceptable salt. If used, a salt of the drug compound should be both pharmacologically and pharmaceutically acceptable, but nonpharmaceutically acceptable salts may conveniently be used to prepare the free active compound and are not excluded from the scope of this invention. Pharmacologically and pharmaceutically acceptable salts can be prepared by reaction of the drug with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

Examples of hydrophobic drug molecules that may be encapsulated within the multi-arm block copolymer in embodiments comprising a hydrophobic core region include, but are not limited to, abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allylsulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene, baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butylated hydroxyanisole, butylated hydroxytoluene, calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, cournachlor, coumaphos, coumithoate cresyl acetate, crimidine, crufomate, cuprobam, cyamemazine, cyclandelate, cyclarbamate cymarin, cyclosporin A, cypermethril, dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, 3,4-di-[1-methyl 6-nitro-3-indolyl]-1H-pyrrole-2,5-dione (MNIPD), dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscournacetate, ethylhydrocupreine, ethyl menthane carboxamide, eugenol, euprocin, exalamide, febarbamate, fenalamide, fenbendazole, fenipentol, fenitrothion, fenofibrate, fenquizone, fenthion, feprazone, fhlpin, filixic acid, floctafenine, fluanisone, flumequine, fluocortin butyl, fluoxymesterone, flurothyl, flutazolam, fumagillin, 5-furftiryl-5-isopropylbarbituric acid, fusaftmgine, glafenine, glucagon, glutethimide, glybuthiazole, griseofulvin, guaiacol carbonate, guaiacol phosphate, halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione, josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone, octaverine, oleandrin, oleic acid, oxazepam, oxazolam, oxeladin, oxwthazaine, oxycodone, oxymesterone, oxyphenistan acetate, paclitaxel, paraherquamide, parathion, pemoline, pentaerythritol tetranitrate, pentylphenol, perphenazine, phencarbamide, pheniramine, 2-phenyl-6-chlorophenol, phenthnethylbarbituric acid, phenytoin, phosalone, O-phthalylsulfathiazole, phylloquinone, picadex, pifarnine, piketopfen, piprozolin, pirozadil, pivaloyloxymethyl butyrate, plafibride, plaunotol, polaprezinc, polythiazide, probenecid, progesterone, promegestone, propanidid, propargite, propham, proquazone, protionamide, pyrimethamine, pyrimithate, pyrvinium pamoate, quercetin, quinbolone, quizalofo-ethyl, rafoxanide, rescinnamine, rociverine, ronnel, salen, scarlet red, siccanin, simazine, simetride, simvastatin, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, tripararol, ursolic acid, valinomycin, verapamil, vinblastine, vitamin A, vitamin D, vitamin E, xenbucin, xylazine, zaltoprofen, and zearalenone.

Examples of charged biologically active agents that can be entrapped within multi-arm block copolymer embodiments having a charged inner core region include cisplatin, lidocaine and its analogues, tolterodine, mitoxantrone, and imatinib (Gleevec).

In embodiments of the block copolymer of the invention having functional groups within either the polypeptide segment or the PEG segment available for covalent attachment to drug molecules, any drug molecule having an available functional group capable of reacting with the functional group of the block copolymer can be used. Such drug molecules include paclitaxel and its analogues, 5-fluorouracil, etoposide, camptothecin and its analogues, vinorelbine and doxorubicin.

III. Pharmaceutical Compositions Comprising the Multi-Arm Block Copolymer

In another aspect, the invention provides pharmaceutical formulations or compositions, both for veterinary and for human medical use, comprising a multi-arm block copolymer as described above and at least one biologically active agent entrapped within the multi-arm block copolymer, preferably within the inner core region defined by the core molecule and the polypeptide segments. As noted previously, incorporation of a hydrophobic drug into a block copolymer structure having a hydrophobic core provides the ability to solubilize the hydrophobic drug, which can enhance the circulating residence time of the drug upon administration to a patient.

The pharmaceutical formulation can include one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, fatty acids and fatty esters, steroids [e.g., cholesterol]), and chelating agents (e.g., EDTA, zinc and other such suitable cations). Other pharmaceutical excipients and/or additives suitable for use in the compositions according to the invention are listed in "Remington: The Science & Practice of Pharmacy," $19^{th}$ ed., Williams & Williams, (1995), the "Physician's Desk Reference," $52^{nd}$ ed., Medical Economics, Montvale, N.J. (1998), and in "Handbook of Pharmaceutical Excipients," $3^{rd}$ Ed., Ed. A. H. Kibbe, Pharmaceutical Press, 2000.

The block copolymers of the invention may be formulated in compositions including those suitable for oral, buccal, rectal, topical, nasal, ophthalmic, or parenteral (including intraperitoneal injection, intravenous injection, subcutaneous injection, and intramuscular injection) administration. The block copolymers can also be used in formulations suitable for inhalation. The compositions can conveniently be presented in unit dosage form and can be prepared by any of the methods well known in the art of pharmacy. All methods include the step of bringing the block copolymer with drug entrapped therein into association with a carrier. In general, the compositions are prepared by bringing the block copolymer/drug formulation into association with a liquid carrier to form a solution or a suspension, or alternatively, bringing the block copolymer/drug formulation into association with formulation components suitable for forming a solid, optionally a particulate product, and optionally shaping or compressing the product into a shaped or compressed delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter. Generally, particles intended for inhalation will typically have a diameter of from about 0.1 microns to 10 microns, preferably from about 1 micron to about 5 microns.

The amount of the biologically active agent or drug in the formulation will vary depending upon the specific drug employed, its molecular weight, and other factors such as dosage form, target patient population, and other considerations, and will generally be readily determined by one skilled in the art. The amount of biologically active agent in the copolymer formulation will be that amount necessary to deliver a therapeutically effective amount of the drug to a patient in need thereof to achieve at least one of the therapeutic effects associated with the drug. In practice, this will vary depending upon the particular drug, its activity, the severity of the condition to be treated, the patient population, the stability of the formulation, and the like. Compositions will generally contain anywhere from about 1% by weight to about 30% by weight drug, typically from about 2% to about 20% by weight drug, and more typically from about 3% to about 15% by weight drug, and will also depend upon the relative amounts of excipients/additives contained in the composition. More specifically, the composition will typically contain at least about one of the following percentages of the entrapped drug: 0.5%, 1%, 2%, 3%, 4%, 5%, 6%, 7%, 8%, 9%, 10%, 12%, 14%, 16%, 18%, 20%, or more by weight.

IV. Methods of Making the Block Copolymer

The multi-arm block copolymers of the invention can be prepared by covalently attaching a preformed polypeptide segment to the core molecule followed by covalently attaching a preformed hydrophilic polymer segment to the terminus of the polypeptide segment. The linkages between the two polymer segments and between the polypeptide segment and the core molecule will depend on the functional groups employed. Typically, the linkages will be amide linkages. However, other types of linkages, such as carbamates, esters, carbonates, and acetals could also be used without departing from the invention.

Alternatively, one or more of the polypeptide or hydrophilic polymer segments can be prepared by directly polymerizing monomer units of the polymer using, for example, a ring-opening polymerization technique. For example, in order to attach a polypeptide to a polyamine core molecule, an N-carboxyanhydride of an amino acid can be formed and directly polymerized onto the polyamine core by ring-opening polymerization in a suitable solvent. Suitable solvents include dimethylformamide (DMF), tetrahydrofuran (THF), dioxane and the like. Exemplary methods for forming an N-carboxyanhydride of an amino acid are illustrated in Examples 1-3. Exemplary ring-opening polymerization techniques for attaching a polypeptide to a polyamine core are illustrated in Examples 4-5. Amino acid reagents, including amino acids having protected β-carboxylic acid groups, are commercially available from Sigma-Aldrich Corporation (St. Louis, Mo.).

In a second step, the product of the first reaction is reacted with monomer units of ethylene oxide in the presence of a base, such as potassium naphthalenide, sodium hydride, sodium or potassium alkoxides, or other strong bases, to attach a poly(ethylene glycol) segment to the polypeptide segment. For the second step, solvents such as tetrahydrofuran, dioxane, or toluene can be used.

A combination of the above methods can also be used to form the block copolymer of the invention. For example, a ring-opening polymerization can be used to form the polypeptide segment followed by covalent attachment of a preformed PEG polymer, as exemplified in Example 6. Typically, if the amino acid residues have pendant functional groups along the alpha carbon chain of the polypeptide segment, the functional groups are maintained in protected form while the polypeptide is attached to the central core molecule and while the hydrophilic polymer is attached to the terminus of the polypeptide chain. Thereafter, any pendant functional groups can be deprotected and used to couple the polypeptide to biologically active agents (see Examples 7-8). As shown in Example 7, a benzyl protecting group can be removed from aspartic acid residues to provide free carboxylic acid groups along the polypeptide chain. The carboxylic acid groups can then be reacted with a biologically active agent, such as the 5-fluorouracil exemplified in Example 8, to form a covalent linkage between the polypeptide segment and the biologically active agent.

V. Methods of Loading the Drug into the Multi-Arm Block Copolymer

There are several methods for entrapping a biologically active agent or drug within the inner core region of the block copolymers of the invention. Obviously, as described above, the drug can be entrapped by covalent attachment of the drug to the polypeptide or PEG chain.

For embodiments relying on other attraction or bonding forces for drug loading, such as hydrophobicity or differences in electrical charge, there are several methods for entrapping a drug. For loading of a drug bearing a charge or a drug containing a metal such as platinum, the copolymer and the drug can simply be mixed in aqueous solution to encourage charge attraction or metal-acid complexing between the drug and the polypeptide segment of the copolymer.

There are three general methods for loading a hydrophobic drug. In a first method, the drug and the copolymer are co-dissolved in an organic solvent and then dried to form a solid product. The solid product is redissolved in aqueous solution and filtered to remove insoluble particles prior to use. In a second method, the drug is suspended in an aqueous solution of the copolymer and subjected to ultrasonication for several hours in order to intimately contact the drug molecules and the hydrophobic cores of the copolymer structures. The solution is then filtered to remove insoluble particles. In a third method, the drug and the polymer are mixed in solid form and heated to about 60° C. to form a melt. The melt is stirred for several hours to encourage intimate mixing of the drug and copolymer. After cooling to room temperature, the formulation is ready for immediate use, further processing, or storage.

VI. Method of Using the Multi-Arm Block Copolymers

As noted above, the multi-arm block copolymers of the invention can be used to solubilize hydrophobic drug molecules in aqueous solution or to entrap and protect charged drug molecules or any drug molecule capable of covalently attaching to the polypeptide or PEG chains. As a result, the copolymer structures of the invention can be used as drug delivery vehicles by entrapping a variety of drugs within the copolymer structure, particularly within the inner core region of the copolymer, and administering a therapeutically effective amount of the multi-arm block copolymer with the biologically active agent entrapped therein to a mammal.

The block copolymers of the invention can be used as drug delivery vehicles for any condition responsive to a drug molecule capable of entrapment within the copolymer structure. Thus, the block copolymers of the invention can be used in pharmaceutical formulations useful for treating any condition responsive to the entrapped drug in mammals, including humans. A preferred condition for treatment is cancer. The method of treatment comprises administering to the mammal a therapeutically effective amount of a composition or formulation containing the multi-arm block copolymer with a drug entrapped therein. The therapeutically effective dosage amount of any specific formulation will vary somewhat from drug to drug, patient to patient, and will depend upon factors such as the condition of the patient, the loading capacity of the block copolymer, and the route of delivery. As a general proposition, a dosage from about 0.5 to about 20 mg/kg body weight, preferably from about 1.0 to about 5.0 mg/kg, will have therapeutic efficacy. When administered conjointly with other pharmaceutically active agents, even less of the block copolymer/drug composition may be therapeutically effective.

The block copolymer/drug composition may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, and by inhalation.

VII. Experimental

The following examples are given to illustrate the invention, but should not be considered in limitation of the invention. Examples 1-3 illustrate a method of forming an N-carboxyanhydride of an amino acid having a benzyl-protected carboxylic acid group. Examples 4-5 illustrate a ring-opening polymerization technique for attaching a polypeptide chain to a polyamine core molecule. Example 6 illustrates a method of attaching a PEG polymer segment to each polypeptide chain to form block copolymer arms attached to a central polyamine core molecule. Example 7 illustrates a technique for deprotecting the pendant carboxylic acid groups spaced along the polypeptide segment of the block copolymer arms. Example 8 illustrates a method of conjugating a biologically active agent to the pendant carboxylic acid groups of the polypeptide segment of the block copolymer arms. Example 9 illustrates a method of forming a metal-acid complex between a metal-containing drug, cisplatin, and the carboxylic acid groups of a poly(aspartic acid) segment. Example 10 illustrates the release rate of the biologically active agent from the conjugate formed in Example 8.

Unless otherwise indicated, all PEG reagents are available from Shearwater Corporation of Huntsville, Ala. All NMR data was generated by a 300 MHz NMR spectrometer manufactured by Bruker.

Example 1

Synthesis of N-Carboxyanhydride (NCA) of L-Aspartic Acid β-Benzyl Ester

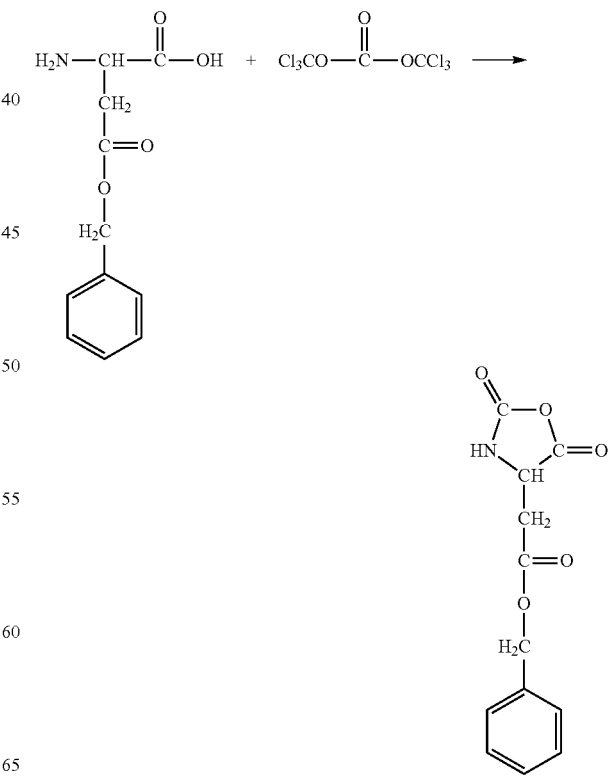

L-aspartic acid β-benzyl ester (Sigma-Aldrich) was suspended in 225 ml of tetrahydrofuran (THF). To the suspension was added approximately 13 g of bis(trichloromethyl) carbonate dissolved in 25 ml of THF, and the mixture stirred at 50° C. until a solution was obtained. The solvent was removed under vacuum. THF was added gradually to the solid residue at 65° C. until the material was completely dissolved. Hexane was added and the solution was gradually cooled to −15° C. The resulting powder was filtered and the product was recrystallized twice and dried at room temperature in vacuo. $^1$H NMR (DMSO-d$_6$): δ 2.98 (d×d, —CHCH$_2$COO—), 4.69 (t, —CHCH$_2$COO—), 5.13 (s, CH$_2$—C$_6$H$_5$—), 7.35 (m, aromatic H).

Example 2

Synthesis of N-Carboxyanhydride (NCA) of L-Glutamic Acid γ-Benzyl Ester

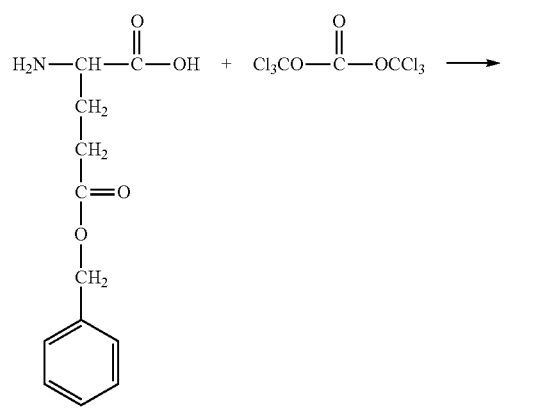

25 grams of L-glutamic acid γ-benzyl ester (Sigma-Aldrich) was suspended in 250 ml of THF. To the suspension was added approximately 12.3 g of bis(trichloromethyl) carbonate dissolved in 25 ml of THF. The mixture was stirred at 50° C. until a transparent solution was obtained and the solvent was removed under vacuum. The solid residue was recrystallized twice from a mixture of THF/hexane and the product dried at room temperature in vacuo. $^1$H NMR (DMSO-d$_6$): δ 1.94 (m, —CHCH$_2$CH$_2$COO—), 2.07 (m, —CHCH$_2$C H$_2$COO—), 4.45 (t, —CHCH$_2$CH$_2$COO—), 5.1 (s, CH$_2$—C$_6$H$_5$—), 7.35 (m, aromatic H).

Example 3

Synthesis of N-Carboxyanhydride of N-ε-Cbz-Lysine

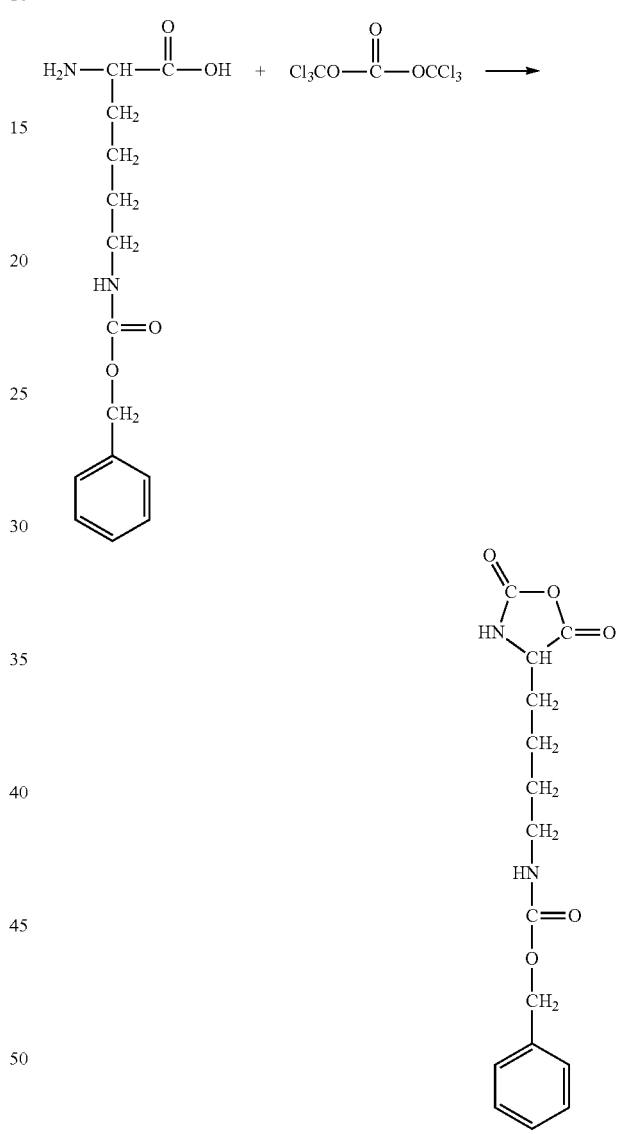

N-ε-Benzyloxycarbonyl-lysine ("N-ε-Cbz-lysine," 50 g, Sigma-Aldrich) was suspended in 500 ml of THF. To the suspension was added 21.2 g of bis(trichloromethyl) carbonate dissolved in 50 ml of THF. The reaction mixture was heated to 50° C. while stirring. After the reaction mixture became transparent (about 15 to 45 minutes), the solution was stirred at 50° C. for another hour. The solution was cooled to room temperature, filtered and the filtrate added to 1,500 ml of hexane. The hexane solution was cooled at −20° C. for 2-3 hours and the resulting precipitate was collected by filtration and further purified by recrystallization from THF/hexane. The product was dried under vacuum. $^1$H NMR (DMSO-d$_6$): δ 1.33 (m, —CHCH$_2$CH$_2$CH$_2$COO—), 1.68 (m, CHCH$_2$CH$_2$CH$_2$CH$_2$COO—), 4.42 (t, —CH̲CH$_2$—), 5.0 (s, CH̲$_2$—C$_6$H$_5$—), 7.3̲1̲ (m, aromatic H).

Example 4

Synthesis of 8-arm Poly(benzyl aspartate)

Example 5

Synthesis of 8-arm Poly(benzyl glutamate)

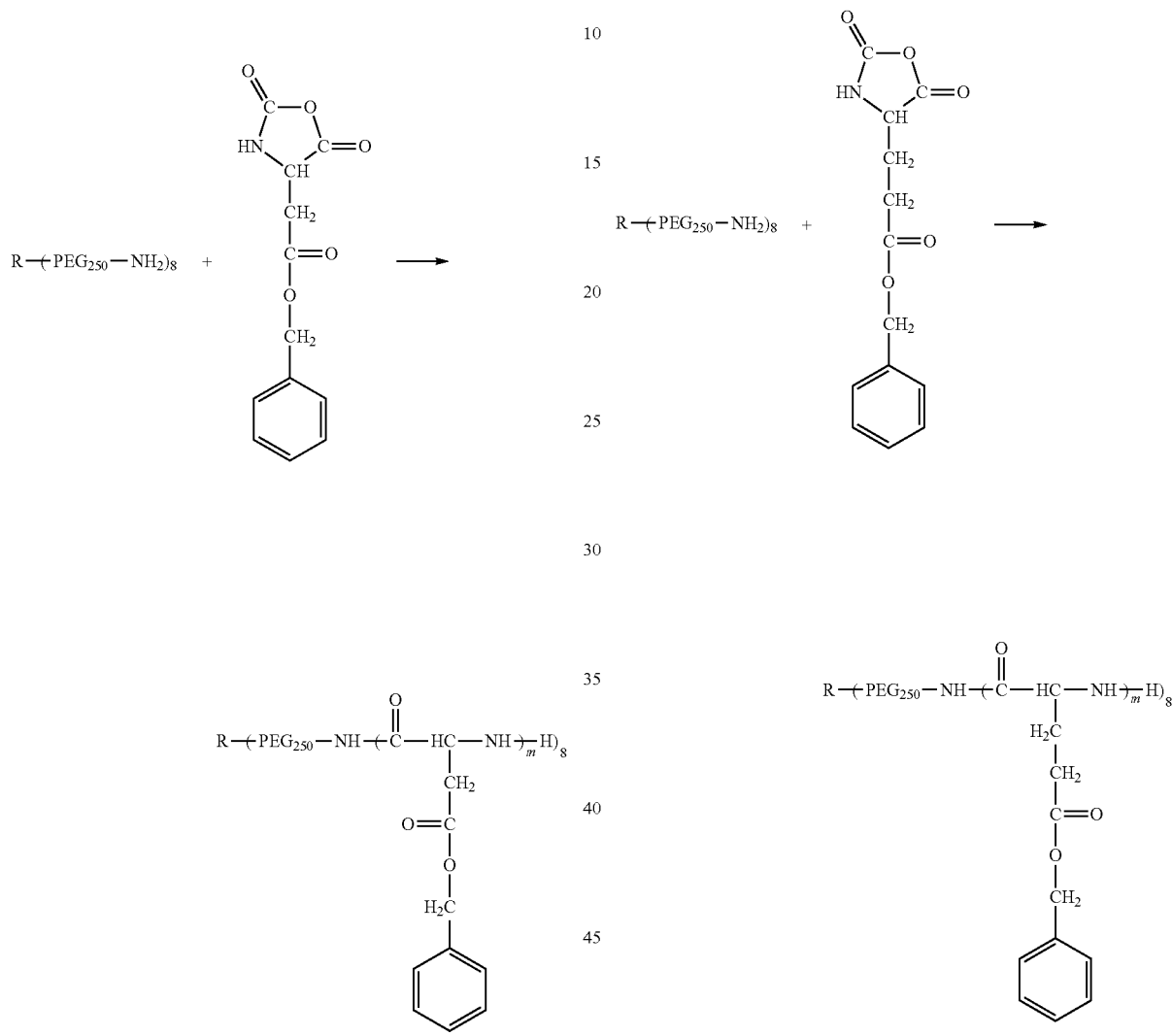

R is hexaglycerol
(m) is an integer from 3-100
(preferably 3-20)

R is hexaglycerine
(m) is an integer from 3-100
(preferably 3-20)

8-arm PEG$_{250}$-amine (0.5 g, total MW 2,000, NOF Corporation, Tokyo, Japan) was dried under vacuum at 60° C. for 2 hours and then dissolved in 10 ml of anhydrous dimethylformamide ("DMF"). To the solution was added a solution of N-carboxyanhydride of benzyl aspartate (10 g) in 10 ml of DMF. The mixture was stirred at 40° C. overnight under N$_2$. The mixture was filtered and the filtrate was added to 200 ml of ether. The precipitate was collected by filtration and dried under vacuum. $^1$H NMR (DMSO-d$_6$): δ 3.5 (m, PEG), δ 2.7 (d×d, —CHCH$_2$COO—), 4.60 (t, —CH̲CH$_2$COO—), 5.10 (s, CH̲$_2$—C$_6$H̲$_5$—), 7.3 (m, aromatic H).

8-arm PEG$_{250}$-amine (0.2 g, total MW 2,000, NOF Corporation, Tokyo, Japan) was azeotropically dried with 200 ml of CHCl$_3$ by distilling off all the solvent under vacuum. The solid residue was then dissolved in 10 ml of anhydrous DMF. To the solution was added a solution of N-carboxyanhydride of benzyl aspartate (5.56 g) in 20 ml of DMF. The mixture was stirred at 40° C. overnight under N$_2$. The product was precipitated with 200 ml of ether. The precipitate was collected by filtration, re-precipitated with DMF/ether, and dried under vacuum. $^1$H NMR (DMSO-d$_6$): δ 3.5 (m, PEG), 2.0 (m, —CHCH$_2$CH$_2$COO—), 4.45 (t, —CH̲CH$_2$CH$_2$COO—), 5.1 (s, CH̲$_2$—C$_6$H̲$_5$—), 7.35 (m, aromatic H).

Example 6

Synthesis of 8-arm Poly(benzyl aspartate)-PEG$_{5000}$

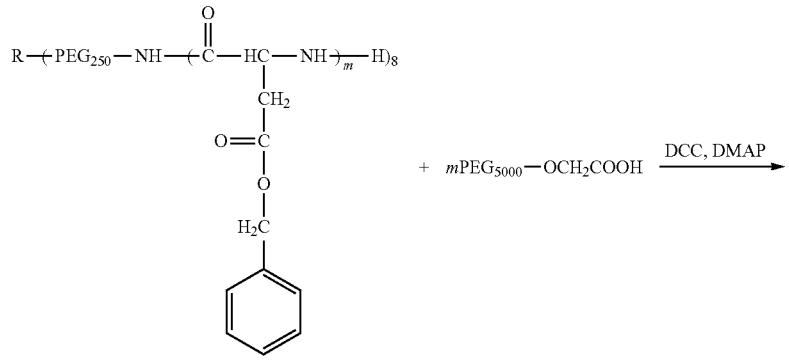

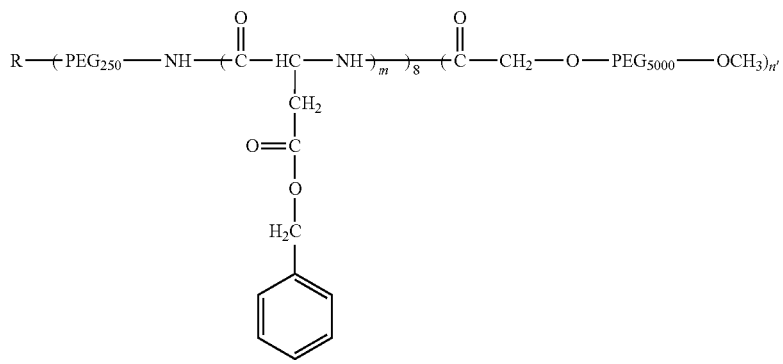

(m) is an integer from 3-100 (preferably 3-20)
(n') is an integer from 2 to 8

8-arm poly(benzyl aspartate) (3 g, from Example 4), mPEG$_{5000}$-CM (3 g, MW 5,000 Da), dicyclohexylcarbodiimide ("DCC," 1.3 g), N,N-dimethylamino pyridine ("DMAP," 0.3 g), and 1-hydroxybenzotriazole ("HOBT," 0.3 g) were dissolved in 30 ml of anhydrous chloroform. To the solution was added freshly distilled triethylamine ("TEA," 1 ml) and the reaction was stirred overnight. The solvent was removed under vacuum. To the residue was added 60 ml of isopropyl alcohol ("IPA") with vigorous stirring. The solid was collected by filtration and washed with ether twice. The product was dried under vacuum. $^1$H NMR (DMSO-d$_6$): δ 3.5 (m, PEG), δ 2.7 (d×d, —CHCH$_2$COO—), 4.60 (t, —CHCH$_2$COO—), 5.10 (s, CH$_2$—C$_6$H$_5$—), 7.3 (m, aromatic H).

Example 7

Preparation of 8-arm Poly(aspartic acid)-PEG$_{5000}$

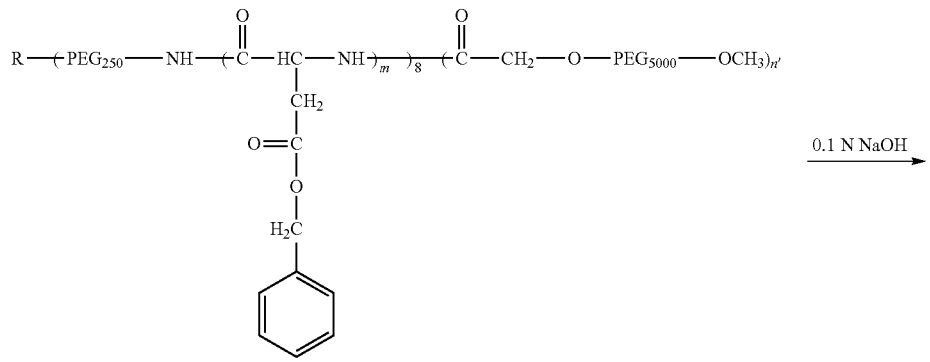

-continued

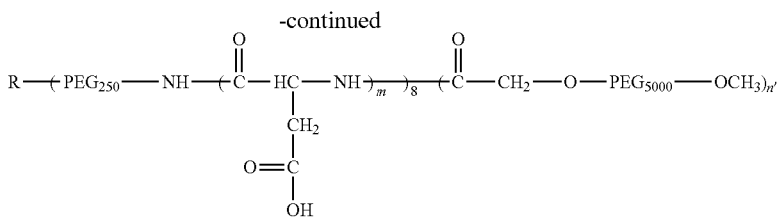

(m) is an integer from 3-100 (preferably 3-20)
(n') is an integer from 2 to 8

The 8-arm poly(benzyl aspartate)-$PEG_{5000}$ (4.5 g, MW 5,000 Da, from Example 6) was dissolved in 0.1 N sodium hydroxide solution and the solution was stirred at room temperature for one hour. After adjustment of pH to 2-3, the solution was dialyzed against water overnight to remove salt, ultrafiltered with a MWCO 50,000 membrane to remove unreacted PEG, washed with water once and then lyophilized. $^1$H NMR ($D_2O$-$d_2$): δ 3.5 (m, PEG), 2.6 (b, —CHC$H_2$COO—), 4.36 (b, —CHCH$_2$COO—).

Example 8

Conjugation of 5-Fluorouracil (5FU) to 8-arm Poly(aspartic acid)-$PEG_{5000}$

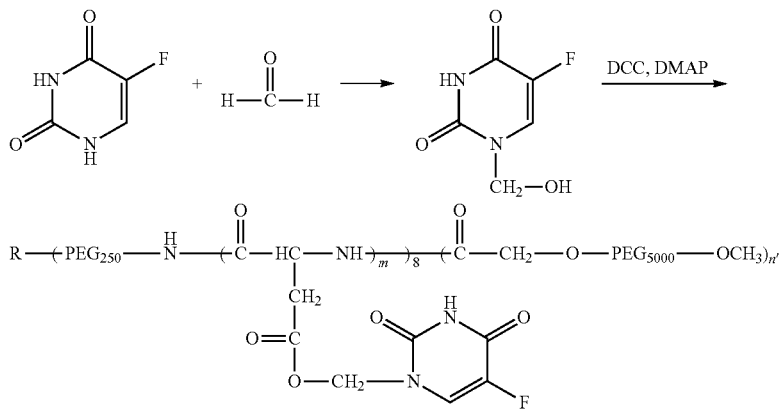

(m) is an integer from 3-100 (preferably 3-20)
(n') is an integer from 2 to 8

5-fluorouracil ("5-FU," 1.51 g, Aldrich) was dissolved in 10 ml of formalin (~40% formaldehyde) and stirred for 1 hour at 60° C. The solvent was removed under vacuum for 1 week. To the residue was added 10 ml of distilled DMF and the solution was stored at −15° C. until used.

8-arm poly(aspartic acid)-$PEG_{5000}$ (0.44 g, from Example 7) was vacuum-dried at 50° C. overnight and 20 ml of distilled chloroform was added. Dicyclohexylcarbodiimide 1.98 g, 4-dimethylaminopyridine 0.276 g, and 1-hydroxybenzotriazole 0.153 g are vacuum-dried at room temperature overnight in a round-bottomed flask, and 10 ml of distilled DMF was added. Both solutions were kept at −15° C. until used. 5FU solution (3 ml, 3.46 mmol) was added to the 8-arm poly (aspartic acid)-$PEG_{5000}$ solution followed by the addition of carbodiimide solution and the mixture was stirred at −15° C. for 5 days. The sample was precipitated in isopropanol. After filtration, the sample was freeze-dried in benzene. $^1$H NMR (DMSO-$d_6$): δ 3.5 (m, PEG), 2.6 (b, —CHCH$_2$COO—), 4.4 (b, —CHCH$_2$COO—), 6.67 (s, —NCH$_2$O—), 8.12 (s, CH in fluorouracil).

Example 9

Incorporation of cis-Diamminodichloro Platinum into 8-arm Poly(aspartic acid)-$PEG_{5000}$ cis-Diamminodichloro platinum (0.012 g, Aldrich) was dissolved in 20 ml of water. 8-arm poly(aspartic acid)-$PEG_{5000}$ (0.056 g, from Example 7) was dissolved in 20 ml of water. The solution was diluted to a final concentration of aspartate group of 10 mM. The cis-diamminodichloro platinum solution was added to the copolymer solution to form three formulations of different concentration ratios of platinum to aspartate. The three formulations prepared had platinum to aspartate ratios of 1:1 (designated as "1:1" in FIG. 4), 1:1.5 (designated as "1:1.5" in FIG. 4), and 1:2 (designated as "1:2" in FIG. 4). The change in UV absorbance at 249 nm versus time was plotted for each formulation and is shown in FIG. 4. As shown in FIG. 4, the absorbance at 249 nm was increased with incubation time at room temperature, indicating that the cis-diamminodichloro platinum complexed with poly(aspartic acid) segments in 8-arm poly(aspartic acid)-$PEG_{5000}$.

Example 10

Hydrolysis Study of Conjugate of 5-fluorouracil (5FU) and 8-arm Poly(aspartic acid)-$PEG_{5000}$ The conjugate of 5-fluorouracil ("5-FU") and 8-aim poly (aspartic acid)-$PEG_{5000}$ (from Example 8) was dissolved in phosphate buffer solutions (0.1M, pH 7.4). The solution was stored at room temperature and 37° C. At timed intervals, the solution was analyzed by HPLC (Ultrahydrogel 250, Waters). The time ($t_{1/2}$) at which 50% of 5-FU was released was 58 hours at room temperature and 13 hours at 37° C.

Many modifications and other embodiments of the invention will come to mind to one skilled in the art to which this invention pertains having the benefit of the teachings presented in the foregoing descriptions and the associated tables. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method comprising:
    (i) covalently attaching a polypeptide segment having a terminus to a central core molecule selected from the group consisting of glycerol, a reducing sugar, pentaerythritol, hydroxypropyl-β-cyclodextrin, and a glycerol oligomer, and wherein the central core molecule bears a hydrophilic ethylene glycol oligomer chain having a molecular weight of about 100 Da to about 5,000 Da; and
    (ii) covalently attaching a hydrophilic polymer segment to the terminus of the polypeptide segment, wherein the hydrophilic polymer segment (a) is selected from the group consisting of poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline and poly(N-acryloylmorpholine), (b) bears a capping group or a functional group selected from the group consisting of alkoxy, hydroxyl, active ester, active carbonate, acetal, aldehyde, aldehyde hydrate, alkyl or aryl sulfonate, halide, disulfide, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxal, dione, mesylate, tosylate and tresylate, to form a unimolecular multi-arm block copolymer having the structure:

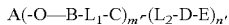

wherein:
    A is a residue of the central core molecule;
    O is oxygen;
    B is the hydrophilic ethylene glycol oligomer chain;
    C is the polypeptide segment;
    D is the hydrophilic polymer segment;
    E is the capping group or functional group;
    $L_1$ is a linkage between B and C formed from a chemical reaction;
    $L_2$ is a linkage between C and D formed from a chemical reaction;
    (m') is 3 to about 25; and
    (n') is 2 to about 25, and (n')≦(m'), wherein the unimolecular multi-arm block copolymer has a total molecular weight of about 10,000 Da to about 200,000 Da.

2. The method of claim 1, wherein the polypeptide segment comprises one or more charged amino acid residues.

3. The method of claim 1, wherein the central core molecule is glycerol.

4. The method of claim 1, wherein the central core molecule is a reducing sugar.

5. The method of claim 4, wherein the reducing sugar is sorbitol.

6. The method of claim 1, wherein the central core molecule is pentaerythritol.

7. The method of claim 1, wherein the central core molecule is hydroxypropyl-β-cyclodextrin.

8. The method of claim 1, wherein the central core molecule a glycerol oligomer.

9. The method of claim 8, wherein the glycerol oligomer is hexaglycerol.

10. The method of claim 1, wherein each $L_1$ is an amide linkage.

11. The method of claim 1, wherein the polypeptide segment comprises residues of amino acids selected from the group consisting of glycine, alanine, valine, leucine, isoleucine, methionine, proline, phenylalanine, tryptophan, serine, threonine, asparagine, glutamine, tyrosine, cysteine, lysine, arginine, histidine, aspartic acid, glutamic acid, and combinations thereof.

12. The method of claim 1, wherein the polypeptide segment comprises residues of charged amino acids.

13. The method of claim 12, wherein the charged amino acids are selected from the group consisting of arginine, lysine, histidine, glutamic acid, aspartic acid, and combinations thereof.

14. The method of claim 1, wherein the polypeptide segment comprises at least one amino acid bearing a functional group.

15. The method of claim 14, wherein the functional group is selected from the group consisting of hydroxyl, active ester, active carbonate, acetal, aldehyde, aldehyde hydrate, alkyl or aryl sulfonate, halide, disulfide, alkenyl, acrylate, methacrylate, acrylamide, active sulfone, amine, hydrazide, thiol, carboxylic acid, isocyanate, isothiocyaniate, maleamide, vinylsulfone, dithiopyridine, vinylpyridine, iodoacetamide, epoxide, glyoxal, dione, mesylate, tosylate, and tresylate.

16. The method of claim 1, wherein each polypeptide segment has a molecular weight of about 100 Da to about 20,000 Da.

17. The method of claim 1, wherein each polypeptide segment has a molecular weight of about 500 Da to about 10,000 Da.

18. The method of claim 1, wherein the hydrophilic polymer segment has a molecular weight of about 100 Da to about 20,000 Da.

19. The method of claim 18, wherein the hydrophilic polymer segment has a molecular weight of about 500 Da to about 10,000 Da.

20. The method of claim 1, wherein the unimolecular multi-arm block copolymer has a total molecular weight of about 20,000 Da to about 80,000 Da.

21. The method of claim 1, wherein said central core molecule has at least four attachment sites available for covalent attachment.

22. The method of claim 1, wherein said central core molecule has at least eight attachment sites available for covalent attachment.

23. The method of claim 1, wherein said central core molecule has 3 to about 25 attachment sites available for covalent attachment.

24. The method of claim 1, wherein hydrophilic polymer segment is a poly(alkylene glycol).

25. The method of claim 24, wherein the poly(alkyene glycol) is poly(ethylene oxide).

26. The method of claim 1, wherein each E is alkoxy.

* * * * *